United States Patent [19]
Tamao et al.

[11] Patent Number: 6,005,128
[45] Date of Patent: Dec. 21, 1999

[54] SILACYCLOPENTADIENE DERIVATIVE

[75] Inventors: Kohei Tamao; Shigehiro Yamaguchi, both of Kyoto; Manabu Uchida, Kanagawa, all of Japan

[73] Assignee: Chisso Corporation, Osaka, Japan

[21] Appl. No.: 09/037,794

[22] Filed: Mar. 10, 1998

[30] Foreign Application Priority Data

| Mar. 11, 1997 | [JP] | Japan | .................................. 9-074500 |
| Dec. 16, 1997 | [JP] | Japan | .................................. 9-363498 |

[51] Int. Cl.⁶ ....................................................... C07F 7/10
[52] U.S. Cl. ........................ 556/406; 534/558; 546/229; 546/14; 556/412
[58] Field of Search .................... 556/406, 412; 534/558; 544/229; 546/14

[56] References Cited

U.S. PATENT DOCUMENTS

| 3,151,140 | 9/1964 | Hubel et al. ............................. 556/406 |
| 3,426,052 | 2/1969 | Hubel et al. ............................. 556/406 |
| 4,104,295 | 8/1978 | Klosowski et al. ...................... 556/406 |
| 5,498,736 | 3/1996 | Tamao et al. ........................... 556/406 |

FOREIGN PATENT DOCUMENTS

| 6-100669 | 4/1994 | Japan . |
| 6-166746 | 6/1994 | Japan . |
| 7-179477 | 7/1995 | Japan . |
| 7-300489 | 11/1995 | Japan . |

OTHER PUBLICATIONS

Uchida et al., "Organic EL Devices Using Silole Derivatives (I)", The Chemical Society of Japan, 70th Spring Annual Meeting pre–manuscript II, p. 700, 2D102.

Uchida et al., "Organic EL Devices Using Silole Derivatives(II)", The Chemical Society of Japan, 70th Spring Annual Meeting pre–manuscript II, p. 701 2D103.

Uchida et al., "Organic Electroluminescence Devices using Silole Derivative (III)", The Chemical Society of Japan, 71st Autumn Annual Meeting pre–manuscript II, p. 32 2p 1α21.

Uchida et al., "Organic Electroluminescence Devices using Silole Derivative (IV)", The Chemical Society of Japan, 71st Autumn Annual Meeting pre–manuscript II, p. 32, 2p 1α22.

Hong et al., "A Novel Lithocenophane Derivative of a Trisgermole Dianion: [Li(thf)(tmeda)][2,3,4,5–Et₄–Ge, Ge–{Li(2,3,4,5–Et₄C₄Ge)₂}C₄GE]", Angew. Chem. Int. Engl. 1996, 35, No. 2, 186.

Freeman et al., "Siloyl Anions and Silole Dianions: Structure of [K([18]crown–6)⁺]₂[C₄Me₄Si²⁻]", Agnew. Chem Int. Ed. Engl. 1996, 35, No. 8, 882.

Hong et al., "Synthesis and Characterization of Two Aromatic Silicon–Containing Dianions:[1] The 2,3,4,5–Tetraphenylsilole Dianion and the 1,1'–Disila–2,2',3,3',4,4',5,5'–octaphenylfulvalene Dianion", Organometallics 1994, 13, 3387–3389.

Deans, et al, "Organosilicon Compounds. Part XIX.* Trimethyl–p–nitro–phenylsilane", Journal of Chemical Society, 1997, 498.

Holmes et al, "Studies on Nitroso Compounds. II. Dimerization of 4–Substituted 2,6–Dichloronitrosobenzenes. An Equilibrium Controlled by the Resonance Effect of para Substituents", The Journal of Organic Chemistry, 30, 3837 (1965).

Alsaidi et al, "Convenient Synthesis of Heteroaryl Phenyl Ethers from Chloropyridines and Chloroquinolines using Phase–Transfer Catalysis", Synthesis, (1980), 921.

Brett, et al., "Sugars with Potential Antiviral Activity. I. Conversion of Hydroxy Compounds to Nitriles", The Journal of Organic Chemistry, 32, 855 (1967).

Friedman, et al., "Dimethylformamide as a Useful Solvent in Preparing Nitriles from Aryl Halides and Cuprous Cyanide; Improved Isolation Techniques", The Journal of Organic Chemistry, 26, 2522 (1961).

M.S. Newman, "α–Napthonitrile* (1–Napthonitrile)", Organic Synthesis, III, 631 (1955).

Songstad, et al., "Isonitriles from Alkyl Halides and Onium Dicyanoargentates", Acta Chem. Scand. 24, 355 (1970).

Bradsher, et al., "Synthesis and Antimicrobial Activity of Some Alkyl 3–Phenanthridinols", The Journal of Organic Chemistry, 22, 500 (1957).

Ulrich, et al, "The Reaction of N–Sulfinylamines and N–Sulfinsulfonamides and Carbonyl Chloride. A New Synthesis of Isocyanates", The Journal of Organic Chemistry, 34, 3200 (1969).

(List continued on next page.)

*Primary Examiner*—Paul F. Shaver
*Attorney, Agent, or Firm*—Wenderoth, Lind & Ponack, L.L.P.

[57] ABSTRACT

The present invention provides a silacyclopentadiene derivative represented by the following Formula (1):

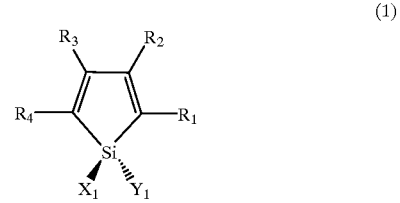

(1)

wherein $X_1$ and $Y_1$ represent independently a halogen atom, an amino group, a hydroxyl group, or an amino group or a hydroxyl group each having a substituent; $R_1$ to $R_4$ represent independently a hydrogen atom, a halogen atom, an alkyl group, an amino group, a silyl group, an aryl group, a cyano group, or the respective groups describe above each having a substituent; out of the groups represented by $R_1$ to $R_4$, those adjacent may be combined with each other to form rings; when $R_1$ and $R_4$ are phenyl groups or when combined are $R_1$ with $R_2$ and $R_3$ with $R_4$ respectively to form benzene rings, $X_1$ and $Y_1$ are not a chlorine atom or a hydroxyl group; and when $R_1$ and $R_4$ are methyl groups, $X_1$ and $Y_1$ are not bromine atoms.

15 Claims, No Drawings

OTHER PUBLICATIONS

Mark W. Farlow, "Hexamethylene Diisocyanate* (Isocyanic acid, hexamethylene ester)", Organic Synthesis, IV, 521 (1963).

Pinnck et al., "An Improved Preparation of Sulfinate Salts and Their Michael Addition to Enones", The Journal of Organic Chemistry, 44, 160 (1979).

Hamada et al., "An Improved Synthesis of Arylsulfonyl Chlorides from Aryl Halides", Synthesis, (1986), 852.

Trost et al., "New Syntheic Reactions. Oxidative Decarboxylation of a α–Methlthiocarboxylic Acids, New Approach of Acyl Anion and Ketene Synthons", Journal of the American Chemical Society, 99, 3101 (1977).

SILACYCLOPENTADIENE DERIVATIVE

BACKGROUND OF THE INVENTION

1. Field of the Invention

The present invention relates to a silacyclopendadiene derivative, more specifically to a silacyclopendadiene derivative, an intermediate therefor and a process for producing the same.

2. Description of the Related Art

It has been tried in various ways in many laboratories to apply π-electron series organic compounds to photo-functional materials or electron-functional materials. Among them, a group of π-electron series organic compounds having a hetero 5-membered ring structure for a basic structure, for example, thiophene or pyrrole is known as one of the typical compound groups. However, a great part of these hetero 5-membered rings is electron-donative, and therefore the characteristic thereof has restricted the application to the materials. This has allowed electron-acceptive compounds to be required.

In recent years, it has been reported that a silacyclopentadiene ring in which a hetero atom is composed of silicon shows an electron-acceptive property, and application thereof to various functional materials is expected. It is reported in, for example, Japanese Patent Application Laid-Open Nos. Hei 6-100669 or Hei 6-166746 that application thereof to conductive polymers is intended. Further, examples in which silacyclopentadiene derivatives have been applied to organic EL elements are reported in The Chemical Society of Japan, 70 Spring Annual Meeting Pre-Manuscript II, pp. 700, 2D102 and pp. 701, 2D103; and 71 Autumn Annual Meeting Pre-Manuscript, pp. 32, 2P1α21 and pp. 32, 2P1α22.

When silacyclopentadiene derivatives are applied to such various functional materials, the introduction of various substituents into optional positions of the silacyclopentadiene rings according to purposes is related to controlling the quality of the compounds and therefore considered to be one of very important techniques for raising the performances of the functional materials.

Conventional synthetic methods for the silacyclopentadiene rings are restricted to specific ones as described in Chemical Review, vol. 90, pp. 215 to 263, 1990, and it has been impossible to freely synthesize various derivatives. Further, examples in which reactive substituents have been introduced into 2- and 5-positions of a silacyclopentadiene ring are shown in Japanese Patent Application Laid-Open Nos. Hei 7-179477 and Hei 7-300489, but the introduction has been restricted to the 2- and 5-positions.

SUMMARY OF THE INVENTION

An object of the present invention is to provide a novel silacyclopentadiene derivative suited for applying to functional materials and an intermediate therefor, and a process for producing the same.

Intensive investigations continued by the present inventors have resulted in finding a novel compound in which a specific functional group is introduced into a silicon atom of a silapentadiyne compound, that is, disubstituted ethynylsilan and that this compound is reacted with an alkaline metal complex to thereby obtain a novel silacyclopentadiene derivative and an intermediate therefor. Further investigations have been continued to come to complete the present invention.

The present invention comprises the following constitutions 1), 2), 3), 4), 5), 6), 7) and 8).

1) A silacyclopentadiene derivative represented by the following Formula (1):

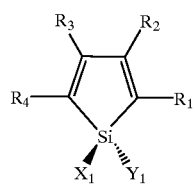

(1)

wherein X1 and Y1 each represent independently a halogen atom, an amino group, a hydroxyl group, or an amino group or a hydroxyl group each having a substituent; $R_1$ to $R_4$ represent independently a hydrogen atom, a halogen atom, an alkyl group, an alkoxy group, an aryloxy group, an amino group, an alkylcarbonyl group, an arylcarbonyl group, an alkoxylcarbonyl group, an aryloxycarbonyl group, an azo group, an alkylazo group, an arylazo group, an alkylcarbonyloxy group, an arylcarbonyloxy group, an alkoxylcarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group or a cyano group, or an alkyl group, an alkoxy group, an aryloxy group, an amino group, an alkylcarbonyl group, an arylcarbonyl group, an alkoxylcarbonyl group, an aryloxycarbonyl group, an alkylcarbonyloxy group, an arylcarbonyloxy group, an alkoxylcarbonyloxy group, an aryloxycarbonyloxy group, a sulfanyl group, a silyl group, a carbamoyl group, an aryl group, a heterocyclic group, an alkenyl group, an alkynyl group, a formyl group or a formyloxy group each having a substituent; out of the groups represented by $R_1$ to $R_4$, those adjacent groups may be combined with each other to form rings; when $R_1$ and $R_4$ are phenyl groups or when combined are $R_1$ with $R_2$ and $R_3$ with $R_4$ respectively to form benzene rings, neither of $X_1$ nor $Y_1$ is a chlorine atom or a hydroxyl group; and when $R_1$ and $R_4$ are methyl groups, $X_1$ and $Y_1$ are not bromine atoms at the same time.

In Formula (1), $R_1$ and $R_4$ each preferably represent independently a hydrogen atom, a halogen atom, an alkyl group, an alkoxy group, an aryloxy group, an amino group, an alkylcarbonyl group, an arylcarbonyl group, an alkoxylcarbonyl group, an aryloxycarbonyl group, an azo group, an alkylazo group, an arylazo group, a sulfinyl group, a sulfonyl group, a sulfanyl group, an aryl group, a heterocyclic group, an alkenyl group, an alkynyl group, a nitro group, a formyl group, a nitroso group, a formyloxy group, an isocyanate group, an isothiocyanate group or a cyano group, or an amino group, a silyl group, an aryl group or a heterocyclic group each having a substituent. $R_2$ and $R_3$ each preferably represent independently a hydrogen atom, a halogen atom, an alkyl group, an alkoxy group, an aryloxy group, an amino group, a silyl group, an aryl group, a heterocyclic group, an alkenyl group, an alkynyl group, an azo group, an alkylazo group, an arylazo group or a cyano group, or an alkyl group, an alkoxy group, an aryloxy group, an amino group, a silyl group, an aryl group, a heterocyclic group, an alkenyl group or an alkynyl group each having a substituent.

$X_1$ and $Y_1$ each represent independently a chlorine atom, a fluorine atom, a dialkylamino group, an alkoxy group or a hydroxyl group, and $R_2$ and $R_3$ each represent a phenyl group or a substituted phenyl group.

Further, the preferred silacyclopentadiene derivative is represented by the following Formula (5):

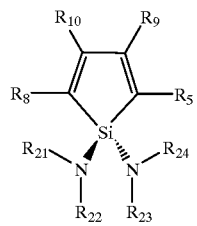

(5)

wherein $R_{21}$ and $R_{24}$ each represent independently an alkyl group or a substituted alkyl group; $R_5$ and $R_8$ each represent independently a hydrogen atom, a halogen atom, an alkyl group, an alkoxy group, an aryloxy group, an amino group, an alkylcarbonyl group, an arylcarbonyl group, an alkoxylcarbonyl group, an aryloxycarbonyl group, an azo group, an alkylazo group, an arylazo group, a sulfinyl group, a sulfonyl group, a sulfanyl group, an aryl group, a heterocyclic group, an alkenyl group, an alkynyl group, a nitro group, a formyl group, a nitroso group, a formyloxy group, an isocyanate group, an isothiocyanate group or a cyano group, or an amino group, a silyl group, an aryl group or a heterocyclic group each having a substituent; and $R_9$ and $R_{10}$ each represent independently an alkyl group, a silyl group, an aryl group, a heterocyclic group or a cyano group, or an alkyl group, a silyl group, an aryl group or a heterocyclic group each having a substituent (provided that $R_9$ and $R_{10}$ may be combined at the terminals to form a ring).

In Formula (5), $R_9$ and $R_{10}$ each represent preferably a phenyl group or a substituted phenyl group.

2) A 1,1-bis(diamino)-2,5-dimetalsilacyclopentadiene derivative represented by the following Formula (2):

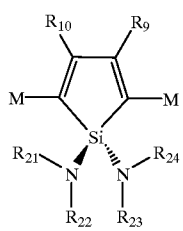

(2)

wherein $R_{21}$ to $R_{24}$ each represent independently an alkyl group or a substituted alkyl group; M represents an alkaline metal; $R_9$ and $R_{10}$ each represent independently an alkyl group, a silyl group, an aryl group, a heterocyclic group, a cyano group, or an alkyl group, a silyl group, an aryl group or a heterocyclic group each having a substituent (provided that $R_9$ and $R_{10}$ may be combined at the terminals to form a ring).

In Formula (2), preferably, $R_9$ and $R_{10}$ each represent independently an alkyl group or a substituted alkyl group, or an aryl group or a substituted aryl group.

3) A 3,3-diamino-3-sila-1,4-pentadiyne derivative [that is, bis(diamino)-diethynylsilane derivative] represented by the following Formula (3):

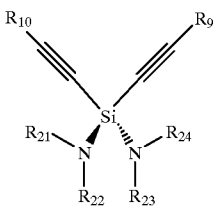

(3)

In Formula (3) described above, $R_9$ and $R_{10}$ each represent independently an alkyl group or a substituted alkyl group, or an aryl group or a substituted aryl group.

4) A process for producing a 1,1-bis(diamino)-3,4-disubstituted-2,5-dimetalsilacyclopentadiyne derivative represented by the following Formula (2) characterized by reacting a 3,3-diamino-3-sila-1,4-pentadiyne derivative represented by the following Formula (3) with an alkaline metal complex:

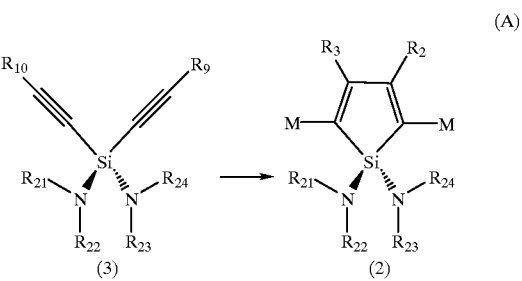

(A)

wherein $R_{21}$ to $R_{24}$, M, $R_9$ and $R_{10}$ are synonymous with those in Formula (2) described previously.

In Formulas (3) and (2) described above, preferably, $R_9$ and $R_{10}$ each represent independently an alkyl group or a substituted alkyl group, or an aryl group or a substituted aryl group.

5) A process for producing a silacyclopentadiene derivative characterized by comprising the steps of:

reacting a 1,1-bis(diamino)-2,5-dimetalsilacyclopentadiene derivative represented by the following Formula (2) with one compound selected from the group consisting of an electrophilic reagent, a metal halide, a complex of a metal halide, boric acid ester and an organic tin compound to introduce active groups Ra into 2- and 5-positions of the above derivative, and subjecting the derivative to hydrolysis, alcoholysis, reduction, oxidation or a coupling reaction to obtain a bis(diamino)silacyclopentadiene derivative represented by Formula (5):

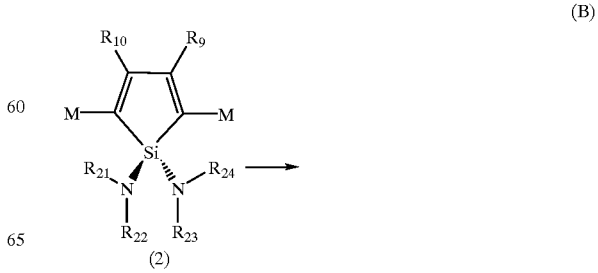

(B)

-continued

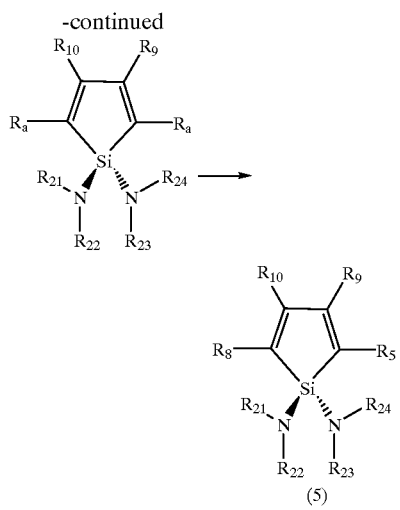

(5)

wherein $R_a$ represents Br, Cl, I, $Si(CH_3)_3$, $Si(C_2H_5)_3$, $Sn(CH_3)_3$, $Sn(C_2H_5)_3$, an alkyl group having 1 to 4 carbon atoms, ZnX, MgX or $B(OR)_3$ (wherein X is halogen, and R is an alkyl group having 1 to 4 carbon atoms); $R_{21}$ to $R_{24}$ each represent independently an alkyl group or a substituted alkyl group; M represents an alkaline metal; $R_5$ and $R_8$ represent independently a hydrogen atom, a halogen atom, an alkyl group, an alkoxy group, an aryloxy group, an amino group, an alkylcarbonyl group, an arylcarbonyl group, an alkoxylcarbonyl group, an aryloxycarbonyl group, an azo group, an alkylazo group, an arylazo group, a sulfinyl group, a sulfonyl group, a sulfanyl group, an aryl group, a heterocyclic group, an alkenyl group, an alkynyl group, a nitro group, a formyl group, a nitroso group, a formyloxy group, an isocyanate group, an isothiocyanate group or a cyano group, or an amino group, a silyl group, an aryl group or a heterocyclic group each having a substituent; and $R_9$ and $R_{10}$ each represent independently an alkyl group, a silyl group, an aryl group, a heterocyclic group or a cyano group, or an alkyl group, a silyl group, an aryl group or a heterocyclic group each having a substituent (provided that $R_9$ and $R_{10}$ may be combined at the terminals to form a ring).

6) A process for producing a silacyclopentadiene derivative characterized by comprising the step of reacting a bis(diamino)silacyclopentadiene derivative represented by the following Formula (5) with hydrochloric acid to produce a dichlorosilacyclopentadiene derivative represented by the following Formula (6):

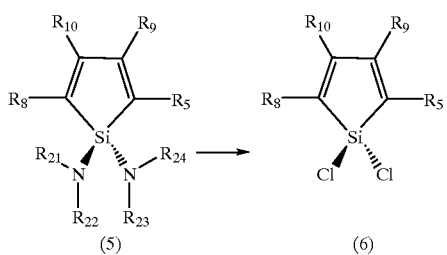

(C)

wherein $R_{21}$ to $R_{24}$, $R_5$, $R_8$, $R_9$ and $R_{10}$ are synonymous with those in Formula (5) described previously.

7) A process for producing a silacyclopentadiene derivative characterized by comprising the step of reacting the bis(diamino)silacyclopentadiene derivative represented by the above Formula (5) with a compound represented by the following Formula (9) to produce a dialkoxysilacyclopentadiene derivative represented by the following Formula (7):

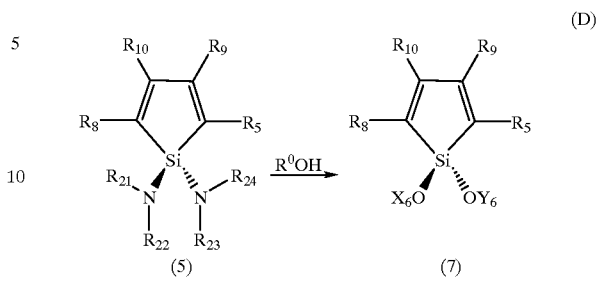

(D)

wherein $R_{21}$ to $R_{24}$, $R_5$, $R_8$, $R_9$ and $R_{10}$ are synonymous with those in Formula (5) described previously; and $R^0$, $X_6$ and $Y_6$ each represent independently an alkyl group or a substituted alkyl group, an aryl group or a substituted aryl group, or a heterocyclic group or a substituted heterocyclic group.

8) A process for producing a silacyclopentadiene derivative characterized by comprising the step of reacting the dichlorosilacyclopentadiene derivative represented by the above Formula (6) with dialkylamine to produce a 1-chloro-1-dialklamino-silacyclopentadiene derivative represented by the following Formula (8):

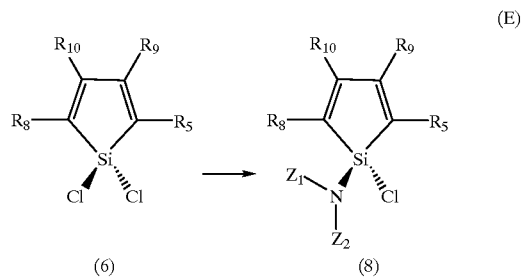

(E)

wherein $R_{21}$ to $R_{24}$, $R_5$, $R_8$, $R_9$ and $R_{10}$ are synonymous with those in Formula (5) described previously; and $Z_1$ and $Z_2$ each represent independently an alkyl group having 1 to 50 carbon atoms.

DETAILED DESCRIPTION OF THE INVENTION

The silacyclopentadiene derivative of the present invention is a compound represented by Formula (1). More specific formulas are Formulas (5), (6), (7) and (8) described above.

Various groups are represented by $X_1$, $Y_1$ and $R_1$ to $R_4$ shown in these formulas as described previously.

$X_1$ and $Y_1$ represent independently a halogen atom, an amino group, a hydroxyl group, or an amino group or a hydroxyl group each having a substituent.

A chlorine atom, a fluorine atom and a bromine atom are shown as the halogen atom.

Shown as the hydroxyl group having a substituent are $OX_6$ and $OY_6$ in Formula (7) (wherein $X_6$ and $Y_6$ each represent an alkyl group or a substituted alkyl group, a cycloalkyl group or a substituted cycloalkyl group, an aryl group or a substituted aryl group, or a heterocyclic group or a substituted heterocyclic group). To be specific, there can be given, alkoxy groups having 1 to 50 carbon atoms (preferably 1 to 20 carbon atoms) such as methoxy, ethoxy, isopropoxy, propoxy, butoxy, secondary butoxy, tertiary butoxy, pentyloxy, cyclopentyloxy, hexyloxy, cyclohexyloxy and decyloxy; aryloxy groups such as phenoxy, biphenyloxy, naphthoxy, anthracenyloxy, terphenyloxy, quarterphenyloxy, phenanthrenyloxy and pyrenyloxy; substituted aryloxy groups such as 3-methylphenyloxy, 4-tertiary-butylphenyloxy and phenylanthracenyloxy; heterocyclic oxy groups such as furyloxy, pyridyloxy, thienyloxy, pyrimidyloxy, pyridanyloxy, triazolyloxy, indolyloxy, carbazolyloxy, phenoxazyloxy, phenothiazyloxy, acridinyloxy, thiadiazolyloxy, thiazolyloxy, oxadiazolyloxy, oxazolyloxy, quinolyloxy, quinoxalyloxy, silacyclopentadienyloxy and pyrrolyloxy; and substituted heterocyclic oxy groups such as benzothiazolyloxy and benzoxazolyloxy.

The amino groups having substituents represented by $R_{21}$ to $R_{24}$ in Formula (5) and $Z_1$ and $Z_2$ in Formula (8) are shown as the amino group having a substituent. The substituents therefor are an alkyl group, a substituted alkyl group, an aryl group, a substituted aryl group, a heterocyclic group and a substituted heterocyclic group each having 1 to 50 carbon atoms. The specific amino group includes dialkylamino groups having 1 to 20 carbon atoms such as dimethylamino, diethylamino, di-normal-propylamino, diisopropylamino, dibutylamino, dicyclopentylamino and dicyclohexylamino; alkenylamino groups such as divinylamino, diallylamino and dibutenylamino; dialkynylamino groups such as diethynylamino, dipropagylamino and bis(phenylethynyl)amino; diarylamino groups such as ditoluylamino, dinaphthylamino, diphenylamino, dibiphenylamino, diphenanthrylamino, phenylnaphthylamino, dianthracenylamino and distyrylamino; and disubstituted amino groups such as dipyridylamino, dihydrofurylamino, dihydropyrenylamino, dioxanylamino, dithienylamino, difurylamino, dioxazolylamino, dioxadiazolylamino, dithiazolylamino, dithiadiazolylamino, diquinolylamino, diquinoxaloylamino, dibenzothienylamino, dibenzothiazolylamino, diindolylamino and disilacyclopentadienylamino.

Further, these substituents may be combined with each other at optional positions to form rings.

The following groups can be given as $R_1$ to $R_4$: a hydrogen atom; a halogen atom such as bromine and chlorine; an alkyl group such as methyl, ethyl, normal propyl, isopropyl and tertiary butyl; a cycloalkyl group such as cyclopentyl and cyclohexyl; an alkoxy group such as methoxy, ethoxy, propoxy, butoxy, hexyloxy, isopropoxy, isobutoxy, isopentyloxy and tertiary butoxy; an alkenyloxy group such as vinyloxy, allyloxy and butenyloxy; an alkynyloxy group such as ethynyloxy and propenyloxy; an aryloxy group such as phenoxy, naphthoxy, biphenyloxy, phenylacetyloxy, pyrenyloxy, phenanthrenyloxy and terphenyloxy; an alkylcarbonyl group such as acetyl; an arylcarbonyl group such as benzoyl; an alkoxycarbonyl group such as methoxycarbonyl and ethoxycarbonyl; an aryloxycarbonyl group such as phenoxycarbonyl; an alkylcarbonyloxy group such as acetoxy; an arylcarbonyloxy group such as benzoyloxy; an alkoxycarbonyloxy group such as methoxycarbonyloxy; an aryloxycarbonyloxy group such as phenoxycarbonyloxy; a sulfinyl group such as methylsulfinyl and phenylsulfinyl; a sulfonyl group such as methylsulfonyl; a sulfanyl group such as methylsulfanyl; a silyl group; a carbamoyl group; an aryl group such as phenyl, biphenyl, terphenyl, naphthyl, anthracenyl, pyrenyl, toluyl and phenanthrenyl; a heterocyclic group such as thienyl, furyl, silacyclopentadienyl, oxazolyl, oxadiazolyl, thiazolyl, thiadiazolyl, acridinyl, quinolyl, quinoxaloyl, phenanthrolyl, benzothienyl, benzothiazolyl, indolyl, carbazolyl, pyridyl, pyrrolyl, benzoxazolyl, pyrimidyl and imidazolyl; an alkenyl group such as vinyl, allyl and butenyl; an alkynyl group such as ethynyl and propagyl; a nitro group, a formyl group, a nitroso group, a formyloxy group, an isocyano group, a cynate group, an isocyanate group, a thiocyanate group, an isothiocyanate group or a cyano group and the like.

Further, included are an alkyl group having a substituent such as trifuloromethyl and phenylethyl; an alkoxy group having a substituent such as trifluoromethoxy, perfluoroethoxy such as pentafluroethoxy and benzyloxy; a substituted aryloxy group such as 3-methylphenyloxy; an amino group having a substituent such as dimethylamino, diethylamino and diphenyl-amino; an alkylcarbonyl group having a substituent such as phenylacetyl; an alkoxycarbonyl group having a substituent such as trifluoromethoxycarbonyl; an aryloxycarbonyl group having a substituent such as 4-fluorophenyloxycarbonyl; an alkylcarbonyloxy group having a substituent such as phenylacetloxy; an arylcarbonyloxy group having a substituent such as 2-methylphenylcarbonyloxy; an alkoxycarbonyloxy group having a substituent such as methoxyethoxy-carbonyloxy; an aryloxycarbonyloxy group having a substituent such as phenyloxadiazolylpheyloxy-carbonyloxy; a silyl group having a substituent such as trimethylsilyl, dimethyl-tertiary-butylsilyl, trimethoxysilyl and triphenylsilyl; a carbamoyl group having a substituent such as dimethylcarbamoyl and diphenylcarbamoyl; an aryl group having a substituent such as styryl, anisyl, fluorophenyl, diphenylamino-phenyl, dimethylaminophenyl, diethylaminophenyl and pyridylphenyl; a heterocyclic group having a substituent such as phenylpyridyl, bithienyl and phenyloxadiazolyl; an alkynyloxy group having a substituent such as phenylethynyloxy and trimethylsilylethynyloxy; an alkenyl group having a substituent such as styryl; and an alkynyl group having a substituent such as phenylethynyl and trimethylsilylethynyl.

Shown as a starting material or an intermediate in producing the silacyclopentadiene derivative of the present invention are 1,1-bis(disubstituted amino)-2,5-dimetalsilole represented by Formula (2) described previously and 3,3-diamino-sila-1,4-pentadiyne [that is, bis(di-substituted amino)-bis(substituted ethynyl)silane] represented by Formula (3).

To be specific, the groups represented by M, $R_9$, $R_{10}$ and $R_{21}$ to $R_{24}$ include the following ones.

$R_9$ and $R_{10}$ are, among the groups represented by $R_1$ to $R_4$, an alkyl group, an alkoxy group, an aryloxy group, an amino group, an azo group, a silyl group, an aryl group, a heterocyclic group, an alkenyl group, an alkynyl group or a cyano group, or an alkyl group, an alkoxy group, an aryloxy group, an amino group, a silyl group, an aryl group, a heterocyclic group, an alkenyl group or an alkynyl group each having a substituent, or a hydrogen atom or a halogen atom, preferably independently an alkyl group, a silyl group, an aryl group, a heterocyclic group, a cyano group, or an alkyl group, a silyl group, an aryl group or a heterocyclic group each having a substituent, more preferably an alkyl group or a substituted alkyl group, or an aryl group or a substituted aryl group. M represents alkaline metal such as lithium, sodium and potassium.

The silacyclopentadiene derivative of the present invention can be produced by the following process.

(a) Dihalogeno-disubstituted-silane is reacted with a mixture obtained by reacting a derivative of acetylene with alkyl metal such butyl lithium to produce a 3,3-bis-disubstituted amino-3-sila-1,4-pentadiyne derivative (diamino-diethynylsilane derivative) represented by Formula (3) which is an intermediate for the silacyclopentadiene derivative of the present invention.

(b) This 3,3-disubstituted amino-3-sila-1,4-pentadiyne derivative is reacted with an alkaline metal complex to produce 1,1-bis(disubstituted amino)-3,4-disubstituted-2,5-metalsilole represented by Formula (2) by so-called cyclization reaction (Equation A described previously).

(c) This 1,1-bis(disubstituted amino)-3,4-disubstituted-2,5-metalsilole is reacted (described later) with an electrophilic reagent (described later), zinc chloride, metal halide such as magnesium halide or a complex thereof, boric acid ester such as triisopropyl borate, or a reagent such as an organic tin compound to introduce an active group into the 2- and 5-positions. Further, this active group is converted to a desired group by reaction such as hydrolysis, alcoholysis, reduction and coupling, whereby the silacyclopentadiene derivative [bis(disubstituted amino)silacyclopentadiene derivative] of the present invention can be obtained.

The reaction example described above shall schematically be shown below.

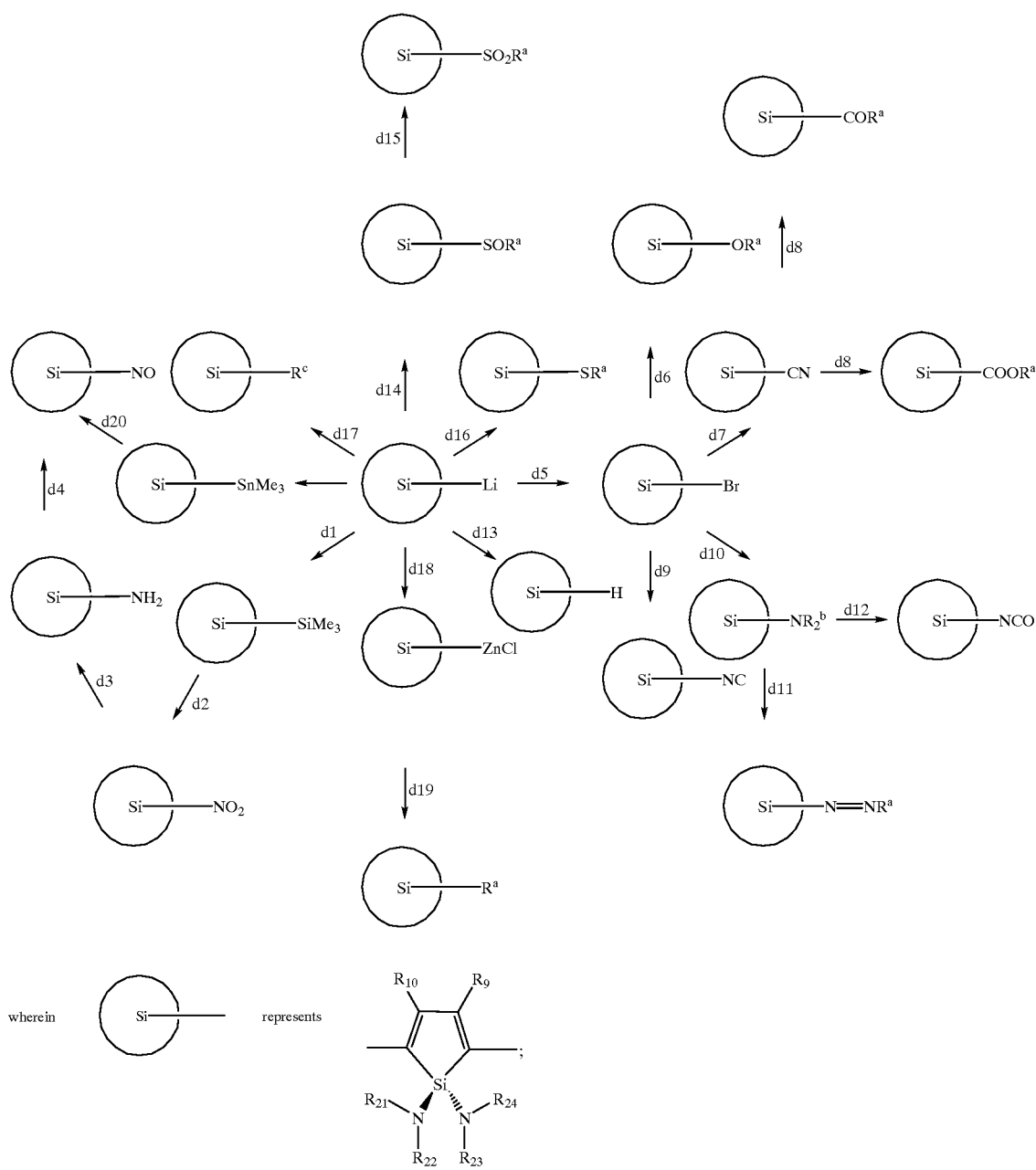

$R^3$ represents a hydrogen atom, an alkyl group, an alkenyl group, an alkynyl group, an aryl group or a heterocyclic group; $R^b$ represents a hydrogen atom or an alkyl group; and $R^c$ represents an alkyl group.

(d) Further, these reactions shall be explained in further detail.

(d1) The 1,1-bis(diamino)-2,5-dimetalsilacyclopentadiene derivative (hereinafter called "the 2,5 dimetal product") represented by Formula (2) can be reacted with a substituted silyl group such as trimethylsilyl chloride and triethylsilyl chloride to convert the metal of the 2- and 5-positions into a substituted silyl group.

(d2) This substituted silyl group can be converted to a nitro group by nitration with acetyl nitrate [refer to F. B. Deans and C.Eaborn,J.Chem.Soc.,1957, 498].

(d3) This nitro group can be converted to an amino group by reduction.

(d4) The amino group can be converted to a nitroso group by oxidation [refer to R. R. Holmes, et al., J.Org.Chem., 30,3837(1965)].

(d5) When bromine is used as an electrophilic reagent for the 2,5 dimetal product, a 1,1-bis(diamino)-2,5-dibromosilacyclopentadiene derivative (hereinafter called "the 2,5 dibromo product") is obtained.

(d6) Then, the 2,5 dibromo product can be reacted with alkoxide or aryloxide to convert bromo atoms into an alkoxy group or an aryloxy group [refer to Synthesis, (1980), 921].

(d7) The 2,5 dibromo product described above can be reacted by substitution reaction with inorganic cyanide to convert bromo atoms into a cyano group. [refer to J.Org.Chem.,32,855(1967) and 26,2522(1961), and Org.Synth.,III,631(1955)].

(d8) This cyano group can be subjected to hydrolysis, alcoholysis, reduction and the like to be converted thereby to an alkylcarbonyl group, an arylcarbonyl group, an alkoxylcarbonyl group, an aryloxycarbonyl group or a formyl group.

(d9) The 2,5 dibromo product described previously can be reacted with a silver (I) cyan complex containing a cation species such as phosphorus and arsenic to be converted thereby to 2,5 isonitrile product [refer to J.Songstad,et al.,Acta.Chem.Scand., 24,355(1970)].

(d10) The 2,5 dibromo product described above can be reacted with $NH_3$ or $PhNH_2$ to be converted thereby to an amino compound or a substituted amino compound [refer to C. K. Bradsher et al.,J.Org.Chem.,22,500 (1957)].

(d11) This amino compound can be reacted with a nitroso compound to form an azo compound.

(d12) This amino compound can be reacted with phosgene or carbon disulfide to be thereby converted an isocyanate compound or an isothiocyanate comound (refer to J.Org.Chem.,34,3200(1969) and Org.Synth.,IV, 521(1963).

(d13) The 2,5 dimetal product can be treated with water to convert the metal into hydrogen.

(d14) The 2,5 dimetal product can be reacted with sulfur dioxide to convert the metal into a sulfinyl group [refer to J.Org.Chem.,44,160(1979)].

(d15) Subsequently, the sulfinyl group can be reacted with sulfuryl chloride to be converted thereby to a sulfonyl group [refer to Synthesis,(1986),852].

(d16) Further, the 2,5 dimetal product can be reacted with sulfur or substituted disulfide to convert the metal into a thiol group or a sulfide group (refer to B. M. Trost,et al., J.Am.Chem.Soc.,99, 3101(1977).

(d17) The 2,5 dimetal product is reacted with dialkylsulfuric acid to convert the 2, 5 dimetal into an alkyl group.

(d18) The 2,5 dimetal product is reacted (transmetallation and the like) with a reagent such as zinc chloride or a complex of zinc chloride, borate, magnesium halide or an organic tin compound to convert the 2,5 dimetal into an active group and (d19) then subjected to a coupling reaction (described later) with various halogenated compounds, whereby the 2- and 5-positions can be converted to an alkyl group, an alkenyl group, an alkynyl group, an aryl group or a heterocyclic group.

(d20) Alkylstannane is reacted with nitrosyl chloride to be converted to a nitroso group (refer to E. H. Bartlett,et al.,J.Chem.Soc.,C,(1970),1717.).

The compound of the present invention can be derived by generally known functional group conversion methods in addition to the above methods.

In the case of the production method by (b) described previously, that is, the equation (A), when groups other than an alkyl group, a silyl group, an aryl group, a heterocyclic group, a cyano group, or an alkyl group, a silyl group, an aryl group or a heterocyclic group each having a substituent, for example, an ester group, an isocyanate group, an isothiocyanate group, a carbonyl group, a formyl group, a sulfonyl group, a sulfinyl group and a nitroso group are introduced into $R_9$ and $R_{10}$ which are groups present in the 3- and 4-positions of the silacyclopentadiene ring, a cyclization reaction in the equation (A) is inhibited. Accordingly, $R_9$ and $R_{10}$ are converted to, for example, an ether group, a thioether group, a disubstituted amino group and a cyano group to carry out the cyclization reaction according to the equation (A), then, they can be converted to the desired groups by a functional group conversion.

(e) The disubstituted amino group of the bis(diamino) silacyclopentadiene derivative represented by Formula (5) obtained in (d) described above can be converted to the desired group of the present invention by, for example, the following method to obtain the silacyclopentadiene derivative of the present invention.

(e-1) The bis(disubstituted amino)silacyclopentadiene derivative represented by Formula (5) is reacted with hydrogen chloride according to the following equation (C) to produce a dichlorosilacyclopentadiene derivative represented by the following Formula (6):

(e-2) The bis(disubstitutedamino) silacyclopentadiene derivative represented by Formula (5) is reacted with a compound represented by $R^oOH$ according to the following equation (D) to produce a dialkoxysilacyclopentadiene derivative represented by the following Formula (7):

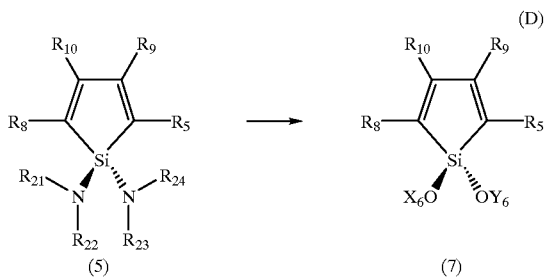

(e-3) The dichlorosilacyclopentadiene derivative represented by Formula (6) obtained in (e-1) described above is reacted with dialkylamine according to the following equation (E) to produce a 1-chloro-1-dialkylaminosilacyclopentadiene derivative represented by the following Formula (8):

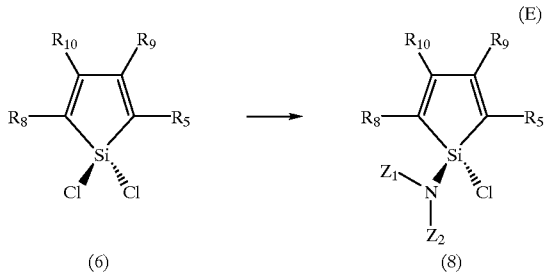

The terminal groups ($R_9$, $R_{10}$ and $R_{21}$ to $R_{24}$) of the 3,3-diamino-3-sila-1,4-pentadiyne derivative represented by Formula (3) are preferably less liable to inhibit the reaction of an alkaline metal complex with acetylene and particularly preferably inert to the alkaline metal complex. Preferably, $R_{21}$ to $R_{24}$ are independently an alkyl group or a substituted alkyl group, and $R_9$ and $R_{10}$ each are independently an alkyl group or a substituted alkyl group, or an aryl group or a substituted aryl group.

The electrophilic reagent used in the production process of the present invention includes substituted silyl chloride such as trimethylsilyl chloride and triethylsilyl chloride, sulfuric acid esters such as dimethyl sulfate and diethyl sulfate, halogens such as bromine and iodine, and acid chlorides.

Metal halide such as magnesium halide or zinc chloride, or a complex thereof, boric acid ester such as triisopropyl borate, or a reagent such as an organic tin compound is substituted for the electrophilic reagent. These reagents are preferably sufficiently dry, and a large amount of moisture makes it difficult to obtain the targeted product.

Bis(diamino)-3,4-disubstituted-2,5-dimetalsilole represented by Formula (3) is reacted with these reagents to subject it to transmetallation and subsequently to a coupling reaction, whereby the silacyclopentadiene derivative can be produced as well.

A yield or a reaction rate is raised in the coupling reaction by using a catalyst. The catalyst used here includes palladium catalysts such as tetrakistriphenylphosphine palladium or dichlorobistriphenylphosphine palladium, or nickel catalysts.

Reaction time shall not specifically be restricted in a series of these reactions, and the reactions can be stopped after the reactions go on satisfactorily. The reactions can be traced by conventional analytical means such as NMR and chromatography to decide the end points of the reactions at an optimum point of time.

The alkaline metal complex used in the production process of the present invention includes, for example, lithium naphthalenide, sodium naphthalenide, potassium naphthalenide, lithium 4,4'-di-tertiary-butyl-2,2'-biphenylide or lithium (N,N-dimethylamino)naphthalenide.

A solvent used for the reactions in the production process of the present invention shall not specifically be restricted as long as it is inert to an alkaline metal and an alkaline metal complex. Usually, ether group solvents such as ethers or tetrahydrofuran are used.

The reaction for forming the silacyclopentadiene ring shown in the equation (A) in (b) described above is carried out preferably in inert gas flow, and argon gas is used. The reaction temperature is preferably low, and the reaction is hard to go on smoothly at 0° C. or room temperatures. A temperature of –4° C. or lower is preferred, and a temperature of –78° C. or lower is particularly preferred. It is described in Japanese Patent Application Laid-Open No. Hei 7-179477 that a reaction temperature in a synthetic reaction of a silacyclopentadiene derivative having a different substituent on silicon is preferably –76° C. to room temperatures, more preferably –40 to 0°. In the case of the present invention, however, the temperatures have to be lower than this temperature range, otherwise side reactions may take place in a certain case.

The silacyclopentadiene derivative of the present invention is useful as a conductive material, an organic EL element or a raw material for electronic materials in electrophotography since it has a reactive substituent on silicon which is a hetero atom and various substituents are introduced into the 2- and 5-positions. The compounds suited to various uses can be synthesized by using them. Further, this silicon atom can be combined as well with polymerizable substances, and polymerization can easily be achieved.

Further, a wide range of the compounds can be synthesized by the production process of the present invention since various substituents can be introduced as well into the 2- and 5-positions of the silacylopentadiene derivative. In conventional production processes, a substituent can be introduced only into a silicon atom of the silacyclopentadiene ring or either of the 2- and 5-positions, but optional substituents can be introduced into both of them at the same time according to the production process of the present invention.

EXAMPLES

The present invention shall specifically be explained below with reference to examples, but the present invention shall not be restricted to the following examples.

Example 1

Synthesis of bis(diethylamino)-bis(phenylethynyl)-silane:

1.6 N normal butyl lithium 205 ml was dropwise added to a solution comprising 33 ml of ethynylbenzene and 300 ml of tetrahydrofuran (hereinafter abbreviated as THF) at 0° C. under nitrogen gas flow, and stirring was continued for 1.5 hour. Dichlorobis(diethylamino)silane 36.5 g and 672 mg of copper cyanide were added to the resulting solution, and stirring was continued at room temperatures for 20 minutes to carry out the reaction. Solid matters precipitated in the reaction liquid were removed by filtering, and then the filtrate was concentrated. Water was added to this concentrate to extract the product with ether. This ether extraction layer was washed with water and then dried on magnesium sulfate. An ether component of this liquid was distilled off, and then the residue was refined by distillation to obtain 52 g of bis(diethylamino)-bis(phenyethynyl)silane. The yield was 93%.

The resulting compound has a boiling point of 230 to 260° C. (vacuum degree: 0.5 Torr), and the measurement results obtained by NMR are shown below:
$^1$HNMR ($C_6D_6$) δ=1.26(t, J=6.9 Hz, 12H), 3.30(q, J=6.9 Hz, 8H). 6.88–7.03(m, 6H), 7.42–7.55(m, 4H).

Example 2

Synthesis of 1,1-bis(diethylamino)-3,4-diphenyl-2,5-bis (trimethylsilyl)silole:

A reaction flask was charged with 280 mg of lithium, 5.13 g of naphthalene and 80 ml of THF, and stirring was continued at room temperatures for 3 hours under an argon atmosphere. A solution comprising 3.75 g of bisdiethylaminobisphenylethynyl-silane and 10 ml of THF was added thereto at −78° C. to continue stirring for one hour, whereby 1,1-bis(diethylamino)-3,4-diphenyl-2,5-dilithiosilole was synthesized.

Subsequently, 5.6 ml of trimethylchlorosilane was added to the reaction liquid obtained above, and stirring was continued for 10 minutes to carry out the reaction. The reaction liquid was left for getting back to room temperatures, and then the solvent was distilled off from the resulting reaction liquid under reduced pressure. Further, naphthalene was removed at 70° C. under reduced pressure to obtain a product. This product was recrystallized from hexane to obtain 4.32 g of 1,1-bis(diethylamino)-3,4-diphenyl-2,5-bis(trimethylsilyl)silole. The yield was 83%.

The compound thus obtained had a melting point of 92 to 94° C. The measurement results obtained by NMR and the result of the elemental analysis are shown below:
$^1$HNMR ($CDCl_3$) δ=0.18(s. 18H), 1.07(t, J=7.0 Hz, 12H), 2.99(q, J=7.0 Hz, 8H), 6.72–6.82(m, 4H), 6.92–7.06(m, 6H).
Molecular formula: $C_{30}H_{48}N_2Si_3$
Theoretical values C: 69.16, H: 9.29, N: 5.38
Experimental values C: 69.09, H: 9.33, N: 5.41

Example 3

Synthesis of 1,1-bis(diethylamino)-3,4-diphenyl-2,5-dimethylsilole:

A reaction flask was charged with 280 mg of lithium, 5.13 g of naphthalene and 80 ml of THF, and stirring was continued at room temperatures for 3 hours under an argon atmosphere. A solution comprising 3.75 g of bisdiethylaminobisphenylethynyl-silane and 10 ml of THF was added thereto at −78° C. to continue stirring for one hour, whereby 1,1-bis(diethylamino)-3,4-diphenyl-2,5-dilithiosilole was synthesized.

Subsequently, 4.16 ml of dimethyl sulfate was added to the reaction liquid obtained above, and stirring was further continued for 10 minutes to carry out the reaction. The reaction liquid was left for getting back to room temperatures, and then the solvent was distilled off from the resulting reaction liquid under reduced pressure. Further, naphthalene was removed at 70° C. under reduced pressure to obtain a product. This product was refined by distillation to obtain 2.83 g of 1,1-bis(diethylamino)-3,4-diphenyl-2,5-dimethylsilole. The yield was 70%.

The compound thus obtained had a melting point of 42 to 43° C. The measurement results obtained by NMR and the result of the elemental analysis are shown below:
$^1$HNMR ($C_6D6$) δ=1.15(t, J=7.0 Hz, 12H), 2.00(s, 6H), 3.11(q, J=7.0 Hz, 8H), 6.90–7.12(m, 10H).
Molecular formula: $C_{26}H_{36}N_2Si$
Theoretical values C: 77.17, H: 8.97, N: 6.92
Experimental values C: 77.09, H: 8.87, N: 6.74

Example 4

Synthesis of 1,1-dichloro-3,4-diphenyl-2,5-bis (trimethylsilyl)silole:

Dry hydrogen chloride gas was blown into a solution comprising 2.22 g of 1,1-bis(diethylamino)-3,4-diphenyl-2, 5-bis(trimethylsilyl)silole and 50 ml of ether at −78° C. for one hour. After distilling ether off from the reaction liquid, dry hexane was added to remove insoluble matters by filtering, and then hexane was distilled off to obtain a product. This product was refined by distillation to obtain 1.55 g of 1,1-dichloro-3,4-diphenyl-2,5-bis(trimethylsilyl) silole. The yield was 81%.

The compound thus obtained had a melting point of 79 to 81° C. The measurement results obtained by NMR and the result of the elemental analysis are shown below:
$^1$HNMR ($C_6D_6$) δ=0.17(s, 18H), 6.72–6.91 (m, 10H).
Molecular formula: $C_{22}H_{28}Si_3Cl_2$
Theoretical values C: 59.03, H: 6.30
Experimental values C: 59.43, H: 6.43

Example 5

Synthesis of 1,1-dichloro-3,4-diphenyl-2,5-dimethylsilole:

The same procedure as in Example 4 was repeated to obtain 1,1-dichloro-3,4-diphenyl-2,5-dimethylsilol, except that 1,1-bis(diethylamino)-3,4-diphenyl-2,5-dimethylsilol obtained in Example 3 was substituted for 1,1-bis (diethylamino)-3,4-diphenyl-2,5-bis(trimethylsilyl)silole. The yield was 80%.

The compound thus obtained had a melting point of 94 to 96° C. The measurement results obtained by NMR and the result of the elemental analysis are shown below:
$^1$HNMR ($C_6D_6$) δ=1.87(s, 6H), 6.66–6.78(m, 4H), 6.82–6.98(m, 6H).
Molecular formula: $C_{18}H_{16}SiCl_2$
Theoretical values C: 65.25, H: 4.87
Experimental values C: 65.45, H: 4.85

Example 6

Synthesis of 1,1-difluoro-3,4-diphenyl-2,5-bis (trimethylsilyl)silole:

Dry hydrogen chloride gas was blown into a 60 ml ether solution of 3.12 g of 1,1-bis(diethylamino)-3,4-diphenyl-2, 5-bis(trimethylsilyl)silole at −78° C. for one hour to carry out the reaction. After distilling ether off from the resulting reaction liquid, dry hexane was added to remove insoluble matters by filtering, and then hexane was distilled off to obtain 1,1-dichloro-3,4-diphenyl-2,5-bis(trimethylsilyl) silole.

Subsequently, 20 ml of ether was added to the reaction liquid obtained above, and 1 ml of pyridinium polyhydrogen fluoride was further added at −78° C. Stirring was continued for 30 minutes to carry out the reaction. After leaving the reaction liquid for getting back to room temperatures to distil ether off, the product was extracted with dry hexane, and hexane contained in the extract was distilled off. Then, the extract was distilled to obtain 1.70 g of 1,1-difluoro-3, 4-diphenyl-2,5-bis(trimethylsilyl)silole. The yield was 69%.

The compound thus obtained had a melting point of 93 to 95° C. The measurement results obtained by NMR and the result of the elemental analysis are shown below:
$^1$HNMR ($C_6D_6$) δ=0.09(s, 18H), 6.72–6.92(m, 10H).
Molecular formula: $C_{22}H_{28}F_2Si_3$
Theoretical values C: 63.72, H: 6.81
Experimental values C: 63.53, H: 6.96

Example 7
Synthesis of 1,1-difluoro-3,4-diphenyl-2,5-dimethylsilole:

The same procedure as in Example 4 was repeated to obtain a crude product of 1,1-dichloro-3,4-diphenyl-2,5-dimethylsilole, except that 1,1-bis(diethylamino)-3,4-diphenyl-2,5-dimethylsilole obtained in Example 3 was substituted for 1,1-bis(diethylamino)-3,4-diphenyl-2,5-bis(trimethylsilyl)silole.

Ether 25 ml was added to this crude product, and 3.70 g of zinc fluoride was further added, followed by continuing stirring for 2 hours to carry out the reaction. Insoluble matters were removed from the reaction liquid thus obtained by filtering, and ether was distilled off from the filtrate. Then, dry hexane was added to remove again insoluble matters, and hexane was distilled off to obtain a product. This product was refined by distillation to thereby obtain 2.49 g of 1,1-difluoro-3,4-diphenyl-2,5-dimethylsilole. The yield was 70%.

The measurement results of the compound thus obtained by NMR are shown below:
$^1$HNMR (CDCl$_3$) δ=1.77(s. 6H), 6.75–6.85(m, 4H), 7.02–7.18(m, 6H).

Example 8
Synthesis of 1,1-dihydroxy-3,4-diphenyl-2,5-bis(trimethylsilyl)silole:

A mixed solution 2.5 ml of THF and water (4:1) was added to 100 mg of 1,1-dichloro-3,4-diphenyl-2,5-bis(trimethylsilyl)silole, and stirring was continued at room temperatures for one hour. Ether was added to the reaction mixture thus obtained to extract the product. The extract was washed with water and dried on sodium sulfate. Sodium sulfate was removed by filtering, and then the filtrate was concentrated to obtain 92 mg of 1,1-dihydroxy-3,4-diphenyl-2,5-bis(trimethylsilyl)silole. The yield was 100%.

The compound thus obtained had a melting point of 205 to 206° C. The measurement results obtained by NMR and the result of the elemental analysis are shown below:
$^1$HNMR (CDCl$_3$) δ=−0.12(s, 18H), 2.52(s, 2H), 6.75–6.86 (m, 4H), 6.98–7.07(m, 6H).
Molecular formula: C$_{22}$H$_{30}$O$_2$Si$_3$
Theoretical values C: 64.33, H: 7.36
Experimental values C: 64.20, H: 7.34

Example 9
Synthesis of 1-fluroro-1-hydroxy-3,4-diphenyl-2,5-bis(trimethylsilyl)silole:

The same procedure as in Example 8 was repeated to obtain 91 mg of 1-fluroro-1-hydroxy-3,4-diphenyl-2,5-bis(trimethylsilyl)silole, except that 1,1-difluoro-3,4-diphenyl-2,5-bis(trimethylsilyl)silole which was obtained in Example 6 was substituted for 1,1-dichloro-3,4-diphenyl-2,5-bis(trimethylsilyl)silole. The yield was 91%.

The compound thus obtained had a melting point of 101 to 103° C. The measurement results obtained by NMR and the result of the elemental analysis are shown below:
$^1$HNMR (CDCl$_3$) δ=−0.10(s, 18H), 2.92(s, 1H), 6.77–6.88 (m, 4H), 6.98–7.09(m, 6H).
Molecular formula: C$_{22}$H$_{29}$OFSi$_3$
Theoretical values C: 64.02, H: 7.08
Experimental values C: 63.65, H: 7.29

Example 10
Synthesis of 1,1-diethoxy-3,4-diphenyl-2,5-bis(trimethylsilyl)silole:

A 4 ml ethanol solution of 261 mg of 1,1-bis(diethylamino)-3,4-diphenyl-2,5-bis(trimethylsilyl)silole and 17 mg of aluminum chloride was stirred at room temperatures for 20 hours. Ethanol was distilled off, and then the residue was refined by means of HPLC (high performance liquid chromatography) to obtain 201 mg of 1,1-diethoxy-3,4-diphenyl-2,5-bis(trimethylsilyl)silole. The yield was 86%.

The compound thus obtained had a melting point of 39 to 40° C. The measurement results obtained by NMR and the result of the elemental analysis are shown below:
$^1$HNMR (CDCl$_3$) δ=−0.13(s, 18H), 1.31(t, J=7.0 Hz, 6H), 3.88(q, J=7.0 Hz, 4H), 6.76–6.84(m, 4H), 6.96–7.08(m, 6H).
Molecular formula: C$_{26}$H$_{38}$O$_2$Si$_3$
Theoretical values C: 66.89, H: 8.20
Experimental values C: 66.85, H: 8.29

Example 11
Synthesis of 1,1-diisoproxy-3,4-diphenyl-2,5-dimethylsilole:

The same procedure as in Example 10 was repeated to obtain 1,1-diisopropoxy-3,4-diphenyl-2,5-dimethylsilole, except that 1,1-bis(diethylamino)-3,4-diphenyl-2,5-dimethylsilole obtained in Example 3 was substituted for 1,1-bis(diethylamino)-3,4-diphenyl-2,5-bis(trimethylsilyl)silole and that 2-propanol was substituted for ethanol. The yield was 64%.

The compound thus obtained had a melting point of 49 to 50° C. The measurement results obtained by NMR and the result of the elemental analysis are shown below:
$^1$HNMR (CDCl$_3$) δ=1.28(d, J=6.2 Hz, 12H), 1.76(s, 6H), 4.25(sep, J=6.2 Hz, 2H), 6.75–6.86(m, 4H), 6.99–7.16(m, 6H).
Molecular formula: C$_{24}$H$_{30}$O$_2$Si
Theoretical values C: 76.14, H: 7.99
Experimental values C: 75.84, H: 7.95

Example 12
Synthesis of 1-chloro-1-diethylamino-3,4-diphenyl-2,5-bis(trimethylsilyl)silole:

Dry hydrogen chloride gas was blown into a 100 ml ether solution of 4.17 g of 1,1-bis(diethylamino)-3,4-diphenyl-2,5-bis(trimethylsilyl)silole at −78° C. for one hour. After distilling ether off, dichloromethane was added, and then 1.3 ml of triethylamine and 1 ml of diethylamine were added in order. After continuing stirring at room temperatures for 20 hours, the solvent was distilled off, and dry hexane was added to remove insoluble matters by filtering. Then, hexane was distilled off from the filtrate to obtain a product. This product was refined by distillation to obtain 3.0 g of 1-chloro-1-diethylamino-3,4-diphenyl-2,5-bis(trimethylsilyl)silole. The yield was 78%.

The compound thus obtained had a melting point of 107 to 108° C. The measurement results obtained by NMR and the result of the elemental analysis are shown below:
$^1$HNMR (C$_6$D$_6$) δ=0.16(s, 18H), 1.15(t, J=7.0 Hz, 6H), 3.12(q, J=7.0 Hz, 4H), 6.78–6.97(m, 10H).
Molecular formula: C$_{26}$H$_{38}$NClSi$_3$
Theoretical values C: 64.48, H: 7.91
Experimental values C: 64.42, H: 8.08, N: 2.76

Example 13
Synthesis of 1,1-bis(diethylamino)-3,4-diphenyl-2,5-dithienylsilole:

Tetramethylethylenediamine complex of zinc chloride was added to 1,1-bis(diethylamino)-3,4-diphenyl-2,5-dilithiosilole synthesized by the same method as in Example 3, and stirring was continued at room temperatures for one hour. A THF solution of 2-bromothiophene and dichlorobistriphenylphosphine palladium were added thereto and refluxed for 10 hours while heating. The reaction liquid was cooled down to room temperature, and then water and toluene were added to remove insoluble matters deposited. Low boiling matters were distilled off under reduced pressure, and the residue was refined by column chromatography to obtain 1,1-bis(diethylamino)-3,4-diphenyl-2,5-dithienylsilole.

Example 14

Synthesis of 1,1-bis(diethylamino)-3,4-diphenyl-2,5-dipyridylsilole:

The same procedure as in Example 13 was repeated, except that 2-bromopyridine was substituted for 2-bromothiophene used in Example 13.

Example 15

Synthesis of 1,1-bis(diethylamino)-3,4-diphenyl-2,5-bis(3-methylphenyl)silole:

The same procedure as in Example 13 was repeated, except that 3-methylbromobenzene was substituted for 2-bromothiophene used in Example 13.

Example 16

Synthesis of 1,1-bis(diethylamino)-3,4-diphenyl-2,5-dibromosilole:

Bromine was dropwise added to 1,1-bis(diethylamino)-3,4-diphenyl-2,5-dilithiosilole synthesized by the same method as in Example 3, and stirring was continued at room temperatures for one hour. Then, a saturated sodium thiosulfate aqueous solution was added to extract the targeted matter with toluene in an organic layer. Low boiling matters were distilled off under reduced pressure, and the residue was refined by column chromatography and recrystallization to obtain 1,1-bis(diethylamino)-3,4-diphenyl-2,5-dibromosilole.

What is claimed is:

1. A silacyclopentadiene derivative represented by the following Formula (1):

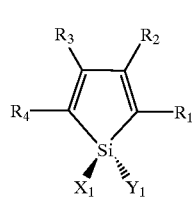

(1)

wherein $X_1$ and $Y_1$ each represent independently a halogen atom, an amino group, a hydroxyl group, or an amino group or a hydroxyl group each having a substituent; $R_1$ to $R_4$ each represent independently a hydrogen atom, a halogen atom, an alkyl group, an alkoxy group, an aryloxy group, an amino group, an alkylcarbonyl group, an arylcarbonyl group, an alkoxylcarbonyl group, an aryloxycarbonyl group, an azo group, an alkylazo group, an arylazo group, an alkylcarbonyloxy group, an arylcarbonyloxy group, an alkoxylcarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group or a cyano group, or an alkyl group, an alkoxy group, an aryloxy group, an amino group, an alkylcarbonyl group, an arylcarbonyl group, an alkoxylcarbonyl group, an aryloxycarbonyl group, an alkylcarbonyloxy group, an arylcarbonyloxy group, an alkoxycarbo- nyloxy group, an aryloxycarbonyloxy group, a sulfanyl group, a silyl group, a carbamoyl group, an aryl group, a heterocyclic group, an alkenyl group, an alkynyl group, a formyl group or a formyloxy group each having a substituent; out of the groups represented by $R_1$ to $R_4$, those adjacent to each other may be combined with each other to form rings; when $R_1$ and $R_4$ are phenyl groups or when combined are $R_1$ with $R_2$ and $R_3$ with $R_4$ respectively to form benzene rings, neither of $X_1$ nor $Y_1$ is a chlorine atom or a hydroxyl group; and when $R_1$ and $R_4$ are methyl groups, $X_1$ and $Y_1$ are not bromine atoms at the same time.

2. The silacyclopentadiene derivative as described in claim 1, wherein $R_1$ and $R_4$ represent independently a hydrogen atom, a halogen atom, an alkyl group, an alkoxy group, an aryloxy group, an amino group, an alkylcarbonyl group, an arylcarbonyl group, an alkoxylcarbonyl group, an aryloxycarbonyl group, an azo group, an alkylazo group, an arylazo group, a sulfinyl group, a sulfonyl group, a sulfanyl group, an aryl group, a heterocyclic group, an alkenyl group, an alkynyl group, a nitro group, a formyl group, a nitroso group, a formyloxy group, an isocyanate group, an isothiocyanate group or a cyano group, or an amino group, a silyl group, an aryl group or a heterocyclic group each having a substituent, $R_2$ and $R_3$ preferably represent independently a hydrogen atom, a halogen atom, an alkyl group, an alkoxy group, an aryloxy group, an amino group, a silyl group, an aryl group, a heterocyclic group, an alkenyl group, an alkynyl group, an azo group, an alkylazo group, an arylazo group or a cyano group, or an alkyl group, an alkoxy group, an aryloxy group, an amino group, a silyl group, an aryl group, a heterocyclic group, an alkenyl group or an alkynyl group each having a substituent.

3. The silacyclopentadiene derivative as described in claim 2, wherein $X_1$ and $Y_1$ represent independently a chlorine atom, a fluorine atom, a dialkylamino group, an alkoxy group or a hydroxyl group, and $R_2$ and $R_3$ each represent a phenyl group or a substituted phenyl group, with the proviso that when $R_1$ and $R_4$ are phenyl groups, neither of $X_1$ nor $Y_1$ is a chlorine atom or a hydroxyl group.

4. A silacyclopentadiene derivative represented by the following Formula (5):

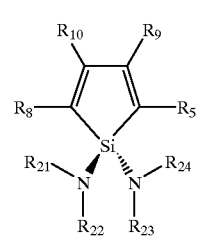

(5)

wherein $R_{21}$ and $R_{24}$ each represent independently an alkyl group or a substituted alkyl group; $R_5$ and $R_8$ represent independently a hydrogen atom, a halogen atom, an alkyl group, an alkoxy group, an aryloxy group, an amino group, an alkylcarbonyl group, an arylcarbonyl group, an alkoxylcarbonyl group, an aryloxycarbonyl group, an azo group, an alkylazo group, an arylazo group, a sulfinyl group, a sulfonyl group, a sulfanyl group, an aryl group, a heterocyclic group, an alkenyl group, an alkynyl group, a nitro group, a formyl group, a nitroso group, a formyloxy group, an isocyanate group, an isothiocyanate group or a cyano group, or an amino group or a silyl group each having a substituent; and $R_9$ and $R_{10}$ represent independently an alkyl group, a silyl group, an aryl group, a heterocyclic group or a cyano group, or an alkyl group, a silyl group, an aryl group or a heterocyclic group each having a substituent (provided that $R_9$ and $R_{10}$ may be combined at the terminals to form a ring).

5. The silacyclopentadiene derivative as described in claim 4, wherein $R_9$ and $R_{10}$ in Formula (5) each represent a phenyl group or a substituted phenyl group.

6. A 1,1-bis(diamino)-2,5-dimetalsilacyclopentadiene derivative represented by the following Formula (2):

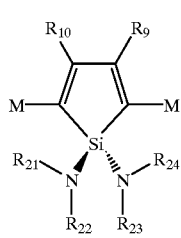

(2)

wherein $R_{21}$ to $R_{24}$ represent independently an alkyl group or a substituted alkyl group; M represents an alkaline metal; $R_9$ and $R_{10}$ represent independently an alkyl group, a silyl group, an aryl group, a heterocyclic group, a cyano group, or an alkyl group, a silyl group, an aryl group or a heterocyclic group each having a substituent (provided that $R_9$ and $R_{10}$ may be combined at the terminals to form a ring).

7. The 1,1-bis(diamino)-2,5-dimetalsilacyclopentadiene derivative as described in claim 6, wherein $R_9$ and $R_{10}$ in Formula (2) represent independently an alkyl group or a substituted alkyl group, or an aryl group or a substituted aryl group.

8. A 3,3-diamino-3-sila-1,4-pentadiyne derivative represented by the following Formula (3):

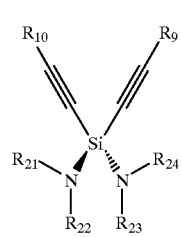

(3)

wherein $R_{21}$ to $R_{24}$, $R_9$ and $R_{10}$ are synonymous with those in claim 6.

9. The 3,3-diamino-3-sila-1,4-pentadiyne derivative as described in claim 8, wherein $R_9$ and $R_{10}$ in Formula (3) represent independently an alkyl group or a substituted alkyl group, or an aryl group or a substituted aryl group.

10. A process for producing a 1,1-bis(diamino)-3,4-disubstituted-2,5-dimetalsilacyclopentadiyne derivative represented by the following Formula (2) characterized by reacting a 3,3-diamino-3-sila-1,4-pentadiyne derivative represented by the following Formula (3) with an alkaline metal complex:

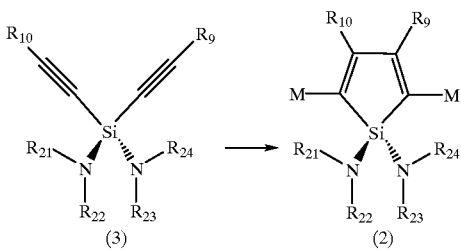

(A)

wherein $R_{21}$ to $R_{24}$, M, $R_9$ and $R_{10}$ are synonymous with those in Formula (2).

11. The process for producing a 1,1-bis(diamino)-3,4-disubstituted-2,5-dimetalsilacyclopentadiyne derivative as described in claim 10, wherein $R_9$ and $R_{10}$ in Formulas (3) and (2) represent independently an alkyl group or a substituted alkyl group, or an aryl group or a substituted aryl group.

12. A process for producing a silacyclopentadiene derivative characterized by comprising the steps of:
 reacting a 1,1-bis(diamino)-2,5-dimetalsilacyclopentadiene derivative represented by the following Formula (2) with one compound selected from the group consisting of an electrophilic reagent, a metal halide, a complex of a metal halide, boric acid ester and an organic tin compound to introduce active groups Ra into 2- and 5-positions of the above derivative, and
 subjecting the derivative to hydrolysis, alcohol-addition decomposition, reduction, oxidation or a coupling reaction to obtain a bis(diamino)silacyclopentadiene derivative represented by Formula (5):

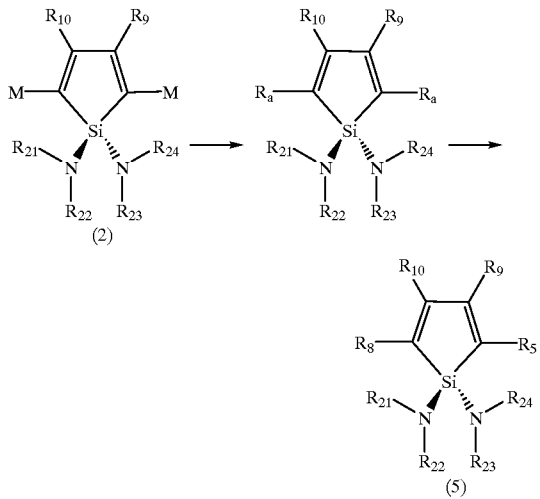

(B)

wherein Ra represents Br, Cl, I, $Si(CH_3)_3$, $Si(C_2H_5)_3$, $Sn(CH_3)_3$, $Sn(C_2H_5)_3$, an alkyl group having 1 to 4 carbon atoms, ZnX, MgX or $B(OR)_3$ (wherein X is halogen, and R is an alkyl group having 1 to 4 carbon atoms); $R_{21}$ to $R_{24}$ represent independently an alkyl group or a substituted alkyl group; M represents an alkaline metal; $R_5$ and $R_8$ represent independently a hydrogen atom, a halogen atom, an alkyl group, an alkoxy group, an aryloxy group, an amino group, an alkylcarbonyl group, an arylcarbonyl group, an alkoxylcarbonyl group, an aryloxycarbonyl group, an azo group, an alkylazo group, an arylazo group, a sulfinyl group, a sulfonyl group, a sulfanyl group, an aryl group, a heterocyclic group, an alkenyl group, an alkynyl group, a nitro group, a formyl group, a nitroso group, a formyloxy group, an isocyanate group, an isothiocyanate group or a cyano group, or an amino group, a silyl group, an aryl group or a heterocyclic group each having a substituent; and $R_9$ and $R_{10}$ represent independently an alkyl group, a silyl group, an aryl group, a heterocyclic group or a cyano group, or an alkyl group, a silyl group, an aryl group or a heterocyclic group each having a substituent (provided that $R_9$ and $R_{10}$ may be combined at the terminals to form a ring).

13. A process for producing a silacyclopentadiene derivative characterized by comprising the step of reacting the bis(diamino)silacyclopentadiene derivative represented by the above Formula (5) with hydrochloric acid to produce a dichlorosilacyclopentadiene derivative represented by the following Formula (6):

wherein $R_{21}$ to $R_{24}$, $R_5$, $R_8$, $R_9$ and $R_{10}$ are synonymous with

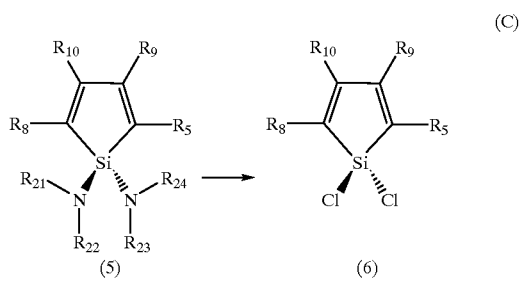

(C)

those in the above Formula (5).

14. A process for producing a silacyclopentadiene derivative characterized by comprising the step of reacting the bis(diamino)silacyclopentadiene derivative represented by the above Formula (5) with a compound represented by the following Formula (9) to produce a dialkoxysilacyclopentadiene derivative represented by the following Formula (7):

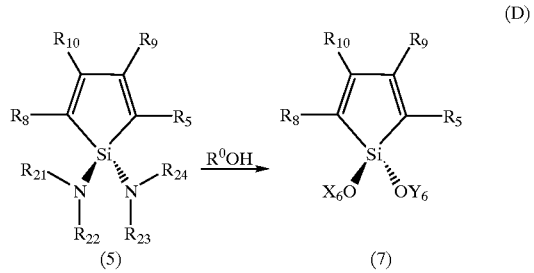

(D)

wherein $R_{21}$ to $R_{24}$, $R_5$, $R_8$, $R_9$ and $R_{10}$ are synonymous with those in the above Formula (5); and $R^0$, $X_6$ and $Y_6$ represent independently an alkyl group or a substituted alkyl group, an aryl group or a substituted aryl group, or a heterocyclic group or a substituted heterocyclic group.

15. A process for producing a silacyclopentadiene derivative characterized by comprising the step of reacting the dichlorosilacyclopentadiene derivative represented by the above Formula (6) with dialkylamine to produce a 1-chloro-1-dialklamino-silacyclopentadiene derivative represented by the following Formula (8):

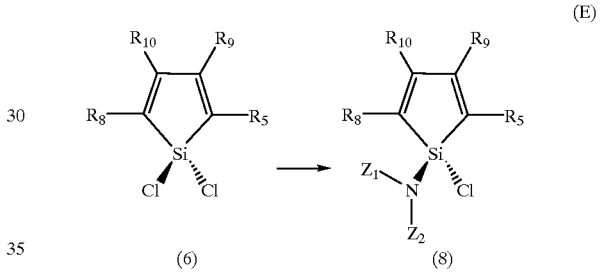

(E)

wherein $R_{21}$ to $R_{24}$, $R_5$, $R_8$, $R_9$ and $R_{10}$ are synonymous with those in the above Formula (5); and $Z_1$ and $Z_2$ represent independently an alkyl group having 1 to 50 carbon atoms.

* * * * *